(12) United States Patent
Kremminger

(10) Patent No.: US 6,894,162 B2
(45) Date of Patent: May 17, 2005

(54) INTERMEDIATES IN CEPHALOSPORIN PRODUCTION

(75) Inventor: Peter Kremminger, Kundl (AT)

(73) Assignee: Sandoz GmbH, Kundl (AT)

( * ) Notice: Subject to any disclaimer, the term of this patent is extended or adjusted under 35 U.S.C. 154(b) by 28 days.

(21) Appl. No.: 10/363,962

(22) PCT Filed: Sep. 10, 2001

(86) PCT No.: PCT/EP01/10447

§ 371 (c)(1),
(2), (4) Date: Mar. 7, 2003

(87) PCT Pub. No.: WO02/20532

PCT Pub. Date: Mar. 14, 2002

(65) Prior Publication Data

US 2003/0171577 A1 Sep. 11, 2003

(51) Int. Cl.$^7$ ............................................. C07D 501/34
(52) U.S. Cl. ..................................................... 540/222
(58) Field of Search .......................................... 540/222

(56) References Cited

U.S. PATENT DOCUMENTS

| | | | |
|---|---|---|---|
| 3,912,589 A | 10/1975 | Smith et al. ................... 195/29 |
| 4,122,259 A | 10/1978 | Humber ........................ 544/22 |
| 4,128,715 A | 12/1978 | Sharp ........................... 544/22 |
| 4,258,183 A | 3/1981 | Humber et al. ................ 544/22 |
| 4,267,320 A | * 5/1981 | Gregson et al. ............. 540/222 |
| 4,277,601 A | 7/1981 | Thompson et al. ............ 544/22 |
| 4,284,766 A | 8/1981 | Lang et al. ................... 544/22 |
| 4,562,181 A | 12/1985 | Crisp et al. .................. 514/202 |
| 4,775,750 A | 10/1988 | White et al. ................. 540/222 |
| 4,912,211 A | 3/1990 | Bonfanti ...................... 540/222 |
| 2002/0016456 A1 * | 2/2002 | Tyagi et al. .................. 540/222 |

FOREIGN PATENT DOCUMENTS

| | | |
|---|---|---|
| EP | 053077 | 6/1982 |
| EP | 127541 | 12/1984 |
| EP | 640608 | 3/1995 |
| GB | 2018764 | 10/1979 |
| GB | 2145409 | 3/1985 |
| IT | 1203701 | 2/1989 |
| JP | 05213968 | 8/1993 |
| WO | WO 00/53609 | 9/2000 |
| WO | WO 01/07443 | 2/2001 |
| ZA | 6801104 | 8/1993 |

OTHER PUBLICATIONS

Translation of JP 05–213968.*
Humber, DC, Laing, SB and Weingarten GG, "The Preparation of 3–Caboamoyloxymethyl and 3–Phosphonocarbamoyloxymethyl Cephalosporins", Glaxo Group Research Ltd., Greenford, U.K., pp 38–45 (1980).
Horsak, Chem Abs 109: 230635 (1988) Abstract of CS 245,077.
OS2C2AP0W1C2, Chem Abs 115: 71269 Abstract of PL 151670.

* cited by examiner

Primary Examiner—Mark L. Berch
(74) Attorney, Agent, or Firm—Joseph T. Majka; Gabriel Lopez

(57) ABSTRACT

Cefuroxime in the form of a salt with n-butylamine; and its use for the production of cefuroxime axetil or for the production of the sodium salt of cefuroxime.

8 Claims, No Drawings

INTERMEDIATES IN CEPHALOSPORIN PRODUCTION

The present invention relates to cephalosporins, such as (6R,7R)-3-carbamoyloxymethyl-7-[(Z)-2-furyl-2-methoxyiminoacetamido]-3-cephem-4-carboxylic acid (cefuroxime) and (6R,7R)-3-carbamoyloxymethyl-7-[(Z)-2-furyl-2-methoxyiminoacetamido]-3-cephem-4-carboxylic acid-1-acetoxyethylester (cefuroxime axetil), see e.g. Merck Index, 12$^{th}$ edition, pages 324–325, item 2002, e.g. useful as antimicrobial agent(s). In known pharmaceutical compositions which contain cefuroxime as active ingredient, such as commercially available compositions, the active ingredient exists normally in the form of a sodium salt for parenteral application; and for oral application, it exists in the form of cefuroxime axetil, e.g. in amorphous form.

In one aspect, the present invention provides a process for the production of cefuroxime in a form which may be used in pharmaceutical compositions comprising cefuroxime as an active ingredient, said process comprising the following steps:

A) acylating 7-amino-3-hydroxymethyl-3cephem-4-carboxylic acid in the form of a guanidine or amidine salt with a reactive derivative of (Z)-2-furyl-2-methoxyiminoacetic acid to obtain 7-[(Z)-2-furyl-2-methoxyiminoacetamido]-3-hydroxymethyl-3-cephem-4-carboxylic acid;

B) reacting 7-[(Z)-2-furyl-2-methoxyiminoacetamido]-3-hydroxymethyl-3-cephem-4-carboxylic acid with a carbamoylation agent to obtain cefuroxime;

C) isolating cefuroxime in the form of a salt with n-butylamine; and either

D1) reacting cefuroxime in the form of a salt with n-butylamine, e.g. in a solvent, in the presence of a source of sodium; and isolating cefuroxime in the form of a sodium salt from the reaction mixture; or D2) reacting cefuroxime in the form of a salt with n-butylamine, e.g. in a solvent, with 1-acetoxyethyl bromide in the presence of a base and isolating cefuroxime axetil from the reaction mixture; and optionally, converting cefuroxime axetil in crystalline form into cefuroxime axetil in an amorphous form, or into cefuroxime axetil in the form of a solid solution in a polymer, or cefuroxime axetil in the form of a surface solid (molecular) dispersion on an adsorbent.

Step A) may be carried out as appropriate, e.g. according, e.g. analogously, to a method as conventional; and is preferably carried out as follows:

7-amino-3-hydroxymethyl-3-cephem-4-carboxylic acid (HACA) is dissolved in a suitable solvent in the presence of an amidine or guanidine, preferably an amidine. Suitable solvents are known and preferably include aprotic solvents, which are capable of forming a second phase in combination with water, e.g. chlorinated hydrocarbons, such as dichloromethane; nitriles, such as acetonitrile; ethers, such as tetrahydrofuran, dimethoxyethane; and mixtures of individual solvents, e.g. solvents as mentioned above; preferably dichloromethane. Suitable amidines or guanidines are known and preferably include tetramethyl guanidine, 1,8-diazabicyclo[5.4.0]undec-7-ene (=DBU) and 1,5-diazabicyclo[4.3.0]non-5-ene (=DBN), most preferably tetramethyl guanidine or DBU, e.g. DBU. At least one, or more, preferably 1.02 to 1.1 equivalents of the amidine or guanidine may be used per equivalent of HACA. Production of the solution may be effected at appropriate temperatures, e.g. at temperatures below room temperature, such as −70° C. to −20° C., preferably about −40° C. to −60° C. A solution of HACA in the form of an amidine or guanidine salt may be obtained and may be isolated; or the solution obtained may be used as such for further reaction in step A). A solution of HACA in the form of an amidine or guanidine salt is brought into contact with a reactive derivative of (Z)-2-furyl-2-methoxyiminoacetic acid, e.g. mixed with it. Reactive derivatives of (Z)-2-furyl-2-methoxyiminoacetic acid are known and include, for example, mixed anhydrides and acid halides, e.g. the acid chloride of (Z)-2-furyl-2-methoxyiminoacetic acid. Processes for the production of the acid chloride of (Z)-2-furyl-2-methoxyiminoacetic acid are known; preferably, (Z)-2-furyl-2-methoxyiminoacetic acid is reacted with oxalyl chloride at appropriate temperatures, e.g. ca. 0° C., in a suitable solvent, e.g. one of the above-mentioned solvents for the production of a salt of HACA with an amidine or guanidine, preferably methylene chloride, e.g. in combination with a small amount of dimethylformamide, e.g. 6 to 15% based on the amount of methylene chloride. Preferably, at least 1 equivalent or more, e.g. 1.05 to 1.1 equivalents of oxalyl chloride are used per equivalent of (Z)-2-furyl-2-methoxyiminoacetic acid.

Preferably at least 1 equivalent or more, e.g. 1.02 to 1.1 equivalents of a reactive derivative of (Z)-2-furyl-2-methoxyiminoacetic acid are used per equivalent of HACA.

Preferably a solution of (Z)-2-furyl-2-methoxyiminoacetic acid in the form of an acid chloride is added to the solution of HACA in the form of a salt.

If a reactive derivative of (Z)-2-furyl-2-methoxyiminoacetic acid is (Z)-2-furyl-2-methoxyiminoacetic acid in the form of an acid halide, a base is added, e.g. a base which is suitable for neutralising the halogen hydrogen compound being released during the reaction, preferably a base which is an amine, e.g. triethylamine. Conveniently at least 1 equivalent or more, for example 1 to 2.5 equivalents of a base may be added per equivalent of (Z)-2-furyl-2-methoxyiminoacetic acid in acid halide form. Preferably a base may be added prior to the addition of the acid halide to the solution of HACA in the form of a salt with an amidine or guanidine. The addition of the acid halide to the solution of HACA in the form of a salt with an amidine or guanidine may be effected at appropriate temperatures, preferably at temperature below 0° C., e.g. at temperatures of −50° C. to −20° C. 7-[(Z)-2-furyl-2-methoxyiminoacetamido]-3-hydroxymethyl-3-cephem-4-carboxylic acid (in the following designated as "7-Furyl-HACA") may be obtained and may be either isolated from the reaction mixture, e.g. as appropriate, e.g. according, e.g. analogously, to a method as conventional; or may be reacted further in step B) without isolation. It is preferable to react further in step B) without isolation.

Step B) may be carried out as appropriate, e.g. according, e.g. analogously, to a method as conventional; and is preferably carried out as follows:

7-Furyl-HACA, dissolved or suspended in a solvent, e.g. in a solvent such as one described in step A), preferably methylene chloride, may be carbamoylated, e.g. reacted with an appropriate carbamoylation reagent, e.g. chlorosulfonyl isocyanate, e.g. in the presence of an acid, e.g. methanesulfonic acid. Carbamoylation in the context of this invention means a reaction of a compound with an appropriate carbamoylation reagent in order to introduce a carbamoyl-group, e.g. a group of —C(O)NH$_2$ into molecules of the compound. At least 1 equivalent or more, e.g. 1.2 to 1.8 equivalents of carbamoylation reagent and ca. 0.4 equivalents and more, e.g. 0.4 to 1.0 equivalents of an acid are used per equivalent of 7-Furyl-HACA; e.g. are added to the solution of 7-Furyl-HACA. The carbamoylation reaction is carried out at appropriate temperatures, e.g. at temperature below 0° C., for example at temperatures of −70° C. to −30° C. After termination of carbamoylation the reaction mixture obtained is treated with water, preferably water in combination with a cosolvent. The cosolvent is preferably a solvent that is readily miscible with water, for example an amide, sulfoxide or urea, such as DMF, dimethylacetamide, dimethylsulfoxide, dimethylethylene urea; an ether such as tetrahydrofuran, dioxane or dimethoxyethane; an alcohol such as methanol, ethanol or isopropanol, most preferably DMF. The carbamoylation reaction mixture is preferably added to water, which optionally contains a cosolvent.

Cefuroxime is obtained and may be isolated from the reaction mixture as appropriate, e.g. according, e.g. analogously, to a method as conventional. Preferably, cefuroxime is transferred from the reaction mixture to a solvent which is suitable for the production of cefuroxime in the form of a salt with n-butylamine, e.g. a solvent such as that described below in the description of the production of cefuroxime in the form of a salt with n-butylamine. This transfer may be effected as appropriate, e.g. according, e.g. analogously, to a method as conventional, and preferably is carried out as follows:

If the solvent, in which the reaction of 7-Furyl-HACA with the carbamoylation reagent has been carried out, is a solvent which is capable of forming a second phase in combination with water, the above-described mixing of water with the reaction mixture, optionally in combination with a cosolvent, results in the formation of two phases.

If the solvent, in which the reaction of 7-Furyl-HACA with the carbamoylation reagent has been carried out, is not capable of forming a second phase in combination with water, a solvent which is capable of forming a second phase in combination with water in an appropriate amount is added to the reaction mixture, so that two phases are formed on the above described mixing with water. A two phase system is thus preferably obtained.

The phases obtained may be separated and the organic phase may be extracted with water, in order to remove salts and inorganic impurities. A solution of cefuroxime in a solvent, which is suitable for the production of cefuroxime in the form of a salt with n-butylamine, is obtained.

Step C) may be carried out as appropriate, e.g. according, e.g. analogously, to a method as conventional; and is preferably carried out as follows:

n-butylamine is added to a solution or suspension of cefuroxime in a solvent, and cefuroxime in the form of a salt with n-butylamine is isolated from the reaction mixture, e.g. in crystalline form.

Cefuroxime in the form of a salt with n-butylamine according to the present invention is referred to hereinafter as "Cefuroxime-but-salt".

Suitable solvents are solvents which are inert under the reaction conditions, e.g. solvents in which cefuroxime is at least partly soluble and in which the Cefuroxime-but-salt is poorly soluble, preferably solvents which are capable of forming a second phase in combination with water, e.g. chlorinated hydrocarbons such as dichloromethane, nitriles such as acetonitrile, ethers such as tetrahydrofuran, dimethoxyethane, or mixtures of individual solvents, e.g. such as mentioned above, most preferably dichloromethane. The amount of n-butylamine which is added to the solution or suspension of cefuroxime is at least 1.0, e.g. 1.0 to 2, such as 1.0 to 1.5, e.g. 1.0 to 1.2 equivalents of n-butylamine per equivalent of cefuroxime. The reaction is carried out at appropriate temperatures, e.g. at a temperature of above, below or room temperature; e.g. and can proceed conveniently at room temperature.

The Cefuroxime-but-salt may precipitate from the reaction mixture thus formed; e.g. in solid form. It is an advantage of the present invention that the Cefuroxime-but-salt may precipitate in crystalline form; and normally precipitates in crystalline form under conditions as described above. Seed crystals may be added to the reaction mixture, e.g. in order to initiate crystallisation. Solvents from the reaction mixture may be evaporated, e.g. in order to increase yields.

Cefuroxime in the form of a salt with n-butylamine is new.

In another aspect, the present invention provides cefuroxime of formula

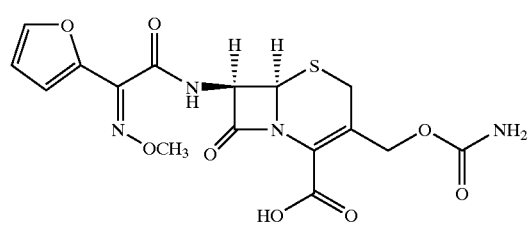

I in the form of a salt with n-butylamine, e.g. in crystalline form.

In another aspect, the present invention provides a process for the production of cefuroxime of formula I in the form of a salt with n-butylamine, comprising adding n-butylamine to a solution or suspension of cefuroxime in a solvent, and isolating cefuroxime in the form of a salt with n-butylamine formed, e.g. in crystalline form, from the reaction mixture.

Crystallisation of an intermediate in the production of a product may result in a high purification effect. Any process according to the present invention may be used on technical scale.

A Cefuroxime-but-salt may be used, for example, for the production of the parenteral form of cefuroxime, namely cefuroxime in the form of a sodium salt, or for the production of an orally available form of cefuroxime, such as the 1-acetoxyethylester of cefuroxime, namely cefuroxime axetil of formula.

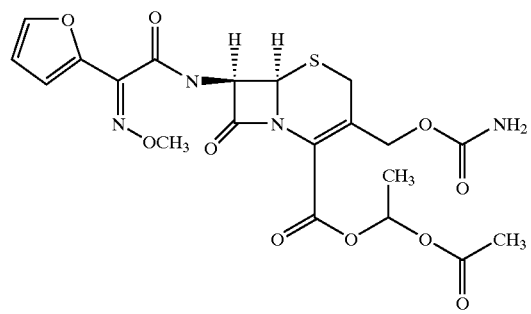

IA

In another further aspect, the present invention provides the use of cefuroxime in the form of a salt with n-butylamine for the production of cefuroxime axetil or for the production of the sodium salt of cefuroxime.

Step D1), the production of cefuroxime in the form of a sodium salt from the Cefuroxime-but-salt may be carried out as appropriate e.g. according, e.g. analogously, to a method as conventional, and is preferably carried out as follows:

The Cefuroxime-but-salt may be reacted in appropriate solvent, e.g. water in combination with a water-miscible solvent, e.g. ethanol and/or acetone, in the presence of an appropriate source of sodium, e.g. the sodium salt of a carboxylic acid, such as ethyl hexanoic acid, diethylacetic acid, acetic acid; lactic acid, to form cefuroxime in the form of a sodium salt which is isolated from the reaction mixture.

For example, the Cefuroxime-but-salt may be dissolved in a solvent and the sodium source may be added to the solution. The reaction may be carried out at temperature as appropriate, e.g. at and above room temperature, preferably 30° C. to 50° C. Cefuroxime in the form of a sodium salt may be obtained and may be isolated as appropriate, e.g. cefuroxime in the form of a sodium salt may precipitate from the reaction mixture, e.g. in crystalline form, and may be isolated as appropriate, e.g. by filtration, centrifugation. In a special embodiment of the present invention the Cefuroxime-but-salt is dissolved in water and the solution obtained is added simultaneously with a Na-lactate solution to a suspension of seed crystals in a Na-lactate solution. Crystalline cefuroxime in the form of a sodium salt may be obtained e.g. in high purity, e.g. in a purity satisfying the requirements of pharmacopoeiae.

In another aspect, the present invention provides a process for the preparation of cefuroxime in the form of a sodium salt, comprising reacting cefuroxime in the form of a salt with n-butylamine in the presence of a source of sodium, and isolating cefuroxime in the form of a sodium salt formed from the reaction mixture.

Step D2), the preparation of cefuroxime axetil from the Cefuroxime-but-salt, may be carried out as appropriate, e.g. according, e.g. analogously, to a method as conventional, e.g. analogously to known processes in which cefuroxime in the form of a sodium salt is used as a starting material to produce cefuroxime axetil; and is preferably carried out as follows:

The Cefuroxime-but-salt may be reacted in a solvent in the presence of a base with 1-acetoxy-ethyl bromide and cefuroxime axetil formed may be isolated from the reaction mixture, preferably in crystalline form.

Appropriate solvents comprise solvents that are inert under the reaction conditions, preferably amides, such as dimethyl acetamide. At least 1 equivalent, preferably 1.5 to 3 equivalents, of 1-acetoxyethyl bromide may be used per equivalent of cefuroxime. Suitable bases include alkaline or alkaline earth carbonates, preferably potassium carbonate, or tertiary amines, e.g. triethylamine. The base may be used in an appropriate amount, e.g. 0.5 to 1.5, preferably 0.9 to 1.2 equivalents of base per equivalent of Cefuroxime-but-salt used. The isolation of cefuroxime axetil formed may be effected according, e.g. analogously to a method as conventional, and is preferably carried out as follows:

The reaction mixture comprising cefuroxime axetil may be mixed with a solvent which is capable of forming a second phase in combination with water, preferably an acetic acid ester, e.g. EtAc. The mixture formed may be extracted with an aqueous solution of a base, e.g. in order to remove inorganic impurities and salts, and cefuroxime axetil may be isolated from the organic phase, preferably by crystallisation. Crystallisation of cefuroxime axetil is preferably effected by adding an anti-solvent, e.g. an ether or a hydrocarbon, preferably diisopropyl ether, to a solution of cefuroxime axetil in a solvent, e.g. an ester such as EtAc, or a solvent mixture, e.g. a mixture of EtAc and dimethyl acetamide. An anti-solvent as used herein is understood to be a solvent wherein a compound, e.g. cefuroxime axetil, is less soluble than in another solvent.

Cefuroxime axetil, which, as is known, may exist in the form of A- and B-diastereomers (A: S-configuration of the axetil group; B: R-configuration of the axetil group) and corresponding A/B mixtures, may be isolated according to the present invention in high purity and in an A/B-isomer ratio which is appropriate for usage as a pharmaceutical, e.g. in a purity and diastereomeric ratio according to the requirements of pharmacopoeiae, e.g. the molar ratio of A/(A+B) diastereomers in the isolated cefuroxime axetil may be in the range of 0.48 to 0.55, such as (around) 0.50.

In another aspect, the present invention provides a process for the production of cefuroxime axetil, e.g. in crystalline form, e.g. in an isomer ratio A/(A+B) of 0.45 to 0.55, comprising reacting cefuroxime in the form of a salt with n-butylamine in a solvent in the presence of a base with 1-acetoxy-ethyl bromide and isolating the cefuroxime axetil formed from the reaction mixture; and, optionally, converting cefuroxime axetil in a crystalline form into cefuroxime axetil in an amorphous form, or into cefuroxime axetil in the form of a solid solution in a polymer, or cefuroxime axetil in the form of a surface solid (molecular) dispersion on an adsorbent.

As is known, cefuroxime e.g. in the form of a sodium salt, may show poor bioavailability when administered orally. Thus, cefuroxime axetil is preferred for use in oral application forms. As is also known, cefuroxime axetil in crystalline form also may show poor oral bioavailability. In oral application forms which are obtainable commercially cefuroxime axetil is thus present in amorphous form.

If cefuroxime axetil is obtained according to the present invention in crystalline form, the crystalline cefuroxime axetil may be converted into an amorphous form, e.g. showing improved bioavailability over a crystalline form, or into a form which is neither crystalline nor amorphous, e.g. into cefuroxime axetil in the form of a solid solution in a polymer, or into cefuroxime axetil in the form of a solid dispersion on an adsorbent. Cefuroxime axetil in the form of a solid solution in a polymer, or cefuroxime axetil in the form of a surface solid (molecular) dispersion on an adsorbent may be bioequivalent to amorphous cefuroxime axetil and therefore may have appropriate bioavailability. Cefuroxime axetil in the form of a solid solution in a polymer, or cefuroxime axetil in the form of a surface solid (molecular) dispersion on an adsorbent are e.g. described in WO00/30647 the content of which is introduced herein by reference. A process for the production of cefuroxime axetil in the form of a solid solution in a polymer or of cefuroxime axetil in the form of a surface solid (molecular) dispersion on an adsorbent includes a process wherein cefuroxime axetil and a polymer which is able to form a solid solution of cefuroxime axetil together with cefuroxime axetil; or a carrier which is able to form a surface solid dispersion with cefuroxime axetil, are dissolved or suspended in organic solvent and (the) solvent is removed. An appropriate weight ratio of cefuroxime axetil:polymer includes a weight ratio of 1:0.1 to 1:0.8, e.g 1:0.35 to 1.0:45; an appropriate weight ratio of cefuroxime axetil:adsorbent includes a weight ratio of 1:0.1 to 1:1.5; e.g. 1:03 to 1:1.3.

A polymer includes preferably a polyvinylpyrrolidone, e.g. a homopolymer such as a povidone, cross-linked povidone, e.g. crospovidone, polyplasdone; and a polyvinylpyrrolidone copolymer; polyethylene glycol, polyethylene oxide, cellulose, preferably a polyvinylpyrrolidone copolymer, such as vinylpyrrolidone-vinylacetate copolymer, e.g. consisting of N-vinyl-2-pyrrolidone and vinyl acetate, e.g. in a random 60:40 ratio.

Appropriate adsorbent includes e.g. material which is able to bind other material on its surface and to form a solid (molecular) dispersion, such as silicium dioxide, preferably colloidal silicium dioxide. Appropriate organic solvent(s) include one single organic solvent or a mixture of organic solvents, e.g. in the presence of water, e.g. a ketone, e.g. acetone, an alcohol, e.g. ethanol; and a halogenated hydrocarbon, e.g. methylene chloride. Preferred organic solvent includes ketones, e.g. in the presence of water, e.g. up to (around) 30% v/v of the organic solvent.

The conversion of crystalline cefuroxime axetil into amorphous cefuroxime axetil may be effected as appropriate, e.g. according, e.g. analogously, to a method as conventional and is preferably effected by dissolving crystalline cefuroxime axetil in appropriate solvent and spray-drying.

In a preferred embodiment, steps A), B) and C) are carried out in a one-pot reaction, i.e. without isolating intermediate products.

In a further preferred embodiment, the production of cefuroxime is effected by starting with HACA in a solvent which is capable of forming a second phase in combination with water, preferably dichloromethane, tetrahydrofuran, dimethoxyethane or acetonitrile, optionally in the presence of an organic amide, sulfoxide, ether or alcohol; or individual mixtures of solvents listed above.

In the following examples all temperatures are in degree Centigrade.

The following abbreviations are used:
DMF: N,N'-dimethylformamide DBU: 1,8-diazabicyclo[5.4.0]undec-7-ene EtAc: ethyl acetate

EXAMPLE 1

Preparation of Cefuroxime in the form of a Salt with n-Butylamine

A) 2-Furyl-2-methoxyimino-acetic acid in the form of the acid chloride 8.2 g of oxalyl chloride are added dropwise at ca. 0° to a solution of 5.12 g of DMF in 60 ml of $CH_2Cl_2$. A white suspension is obtained, which is stirred for ca. 1 hour in an ice bath and is added at below −40° C. to a solution of 10.32 g of 2-furyl-2-methoxyiminoacetic acid in 140 ml of methylene chloride.

B) 7-Amino-3-hydroxymethyl-3-cephem-4-carboxylic acid in the form of a salt with DBU A clear solution is produced from 13.84 g of 7-amino-3-hydroxymethyl-3-cephem-4-carboxylic acid in 120 ml of methylene chloride and 9.32 ml of DBU at −50°. To the solution obtained 19.4 ml of triethylamine are added. To the solution obtained the cold solution obtained under a) is added dropwise at below −35°, 4.06 ml of methanesulfonic acid and 7.0 ml of chlorosulfonyl isocyanate are added dropwise to the reaction mixture obtained, and the resulting reaction mixture is stirred for ca. 30 minutes at ca. −50°. The cold mixture obtained is added dropwise at ca. 30° to a mixture of 100 ml of DMF and 100 ml of water, and the resulting mixture is stirred at ca. 30° and mixed with 160 ml of water. Two phases formed are separated. The organic (methylene chloride) phase is washed with water/DMF and mixed at room temperature with 5.88 ml of n-butylamine. Cefuroxime in the form of a salt with n-butylamine crystallises, is filtrated off, washed with methylene chloride and dried. Yield: 22.4 g.

$^1$H-NMR(DMSO-$d_6$): δ 0.87 (t, 3H, J=7.5 Hz), 1.31 (m, 2H), 1.52 (m, 2H), 2.75 (t, 2H, J=7, 8 Hz), 3.28&3.45(ABq, 2H, J=17.4 Hz), 3.89 (s, 3H), 4.70 &4.81(ABq, 2H, J=12.0 Hz), J=4.7 Hz), 5.65 (d, 1H, J=4.6 Hz), 6.63 (m, 1H), 6.70 (d, 1H, J=3.4 Hz), 7.83 (d, 1H, J=1.1 Hz).

EXAMPLE 2

Production of Cefuroxime Axetil from Cefuroxime in the form of a Salt with n-Butylamine 11.14 g of cefuroxime in the form of a salt with n-butylamine are dissolved at ca. 3° to 5° in 28 ml of dimethyl acetamide. A solution of 7.48 g of acetoxyethyl bromide in 21 ml of dimethyl acetamide is added to the solution obtained, and 1.76 g of $K_2CO_3$ are added in portions over the course of ca. 120 minutes. The resulting mixture is stirred for ca. 30 minutes, diluted with 100 ml of EtAc and aqueous 3% $NaHCO_3$ solution is added. Two phases are formed and are separated and the organic phase is washed with 1 n HCl and 20% aqueous NaCl solution, which contains 2% $NaHCO_3$. The organic phase obtained is mixed with 11 ml of dimethyl acetamide and 28 ml of $H_2O$, and the pH of the mixture obtained is adjusted to ca. 4 by addition of $H_2SO_4$. The two phases formed are separated and the organic phase is mixed with activated carbon, which is filtrated off. From the filtrate obtained solvent is evaporated off and the evaporation residue obtained is mixed with seed crystals. The suspension obtained is mixed with 125 ml of diisopropyl ether and stirred at room temperature. Crystalline cefuroxime axetil is obtained, filtrated off, washed with a mixture of EtAc and diisopropyl ether and dried. Yield: 7.43 g.

EXAMPLE 3

Production of Cefuroxime in the form of a Sodium Salt from Cefuroxime in the form of a Salt with n-Butylamine 27.8 g of cefuroxime in the form of a salt with n-butylamine are dissolved at room temperature in 150 ml of $H_2O$. The solution obtained is treated with activated carbon, the activated carbon is filtrated off and the filtrate obtained is added simultaneously with 175 ml of a 50% sodium lactate solution, over the course of ca. 3 hours at ca. 50° under stirring, to a suspension of 1.25 g of seed crystals of cefuroxime in the form of a sodium salt in 50 g of 25% lactate solution. The suspension obtained is stirred for ca. 15 minutes. Cefuroxime in the form of a sodium salt is obtained, filtrated off, washed with ethanol and dried in a vacuum drying chamber at ca. 40°. Yield: 21.7 g.

What is claimed is:

1. A process for the production of cefuroxime sodium salt or cefuroxime axetil said process comprising the following steps:

A) acylating 7-amino-3-hydroxymethyl-3-cephem-4-carboxylic acid in the form of a amidine salt selected from the group consisting of tetramethyl guanidine, 1,8-diazabicyclo[5.4.0] undec-7-ene and 1,5diazabicyclo[4.3.0]non-5-ene with a reactive derivative of (Z)-2-furyl-2-methoxyimino-acetic acid to obtain 7-[(Z)-2-furyl-2-methoxyiminioacetamide]-3-hydroxymethyl-3-cephem-4-carboxylic acid;

B) reacting 7-[(Z)-2-furyl-2-methoxyiminoacetamido]-3-cephem-4-carboxylic acid with a carbamoylation agent to obtain cefuroxime;

C) isolating cefuroxime in the form of a salt with n-butylamine; and either

D1) reacting cefuroxime in the form of a salt with n-butylamine in the presence of a source of sodium; and isolating cefuroxime in the form of a sodium salt from the reaction mixture; or D2) reacting cefuroxime in the form of a salt with n-butylamine with 1-acetoxyethyl bromide in the presence of a base and isolating cefuroxime axetil from the reaction mixture.

2. A process for the production of cefuroxime axetil comprising reacting cefuroxime in the form of a salt with n-butylamine in a solvent in the presence of a base with 1-acetoxy-ethyl bromide and isolating the cefuroxime axetil formed from the reaction mixture.

3. Cefuroxime in the form of a salt with n-butylamine.

4. A salt according to claim 3 which is crystalline.

5. A process for the production of cefuroxime in the form of a salt with n-butylamine, comprising adding n-butylamine to a solution or suspension of cefuroxime in a solvent, and isolating cefuroxime in the form of a salt with n-butylamine formed from the reaction mixture.

6. A process for the production of cefuroxime in the form of a sodium salt, comprising reacting cefuroxime in the form of a salt with n-butylamine in the presence of a source of sodium, and isolating the cefuroxime in the form of a sodium salt formed from the reaction mixture.

7. A process of claim 1, wherein steps A), B), and C) are carried out in a one-pot reaction.

8. A process of claim 1 wherein crystalline cefuroxime axetil obtained is converted into cefuroxime axetil in an amorphous form, or into cefuroxime axetil in the form of a solid solution in a polymer, or cefuroxime axetil in the form of a surface solid dispersion on an adsorbent.

* * * * *